United States Patent [19]

Uzgiris et al.

[11] 4,191,739
[45] Mar. 4, 1980

[54] ANTIGEN-ANTIBODY REACTION ASSAY EMPLOYING PARTICLE AGGREGATION AND RESISTIVE PULSE ANALYSIS

[75] Inventors: Egidijus E. Uzgiris; Ralph W. De Blois, both of Schenectady, N.Y.

[73] Assignee: General Electric Company, Schenectady, N.Y.

[21] Appl. No.: 842,952

[22] Filed: Oct. 17, 1977

[51] Int. Cl.$^2$ .................... G01N 27/00; G01N 27/26; G01N 31/00; G01N 33/16
[52] U.S. Cl. .................................. 424/12; 23/230 B; 424/8; 424/11; 424/13; 422/56; 422/57; 422/98; 209/3; 209/4
[58] Field of Search ...................... 424/3, 8, 11, 12, 13; 23/230 R, 230 B; 209/3, 4; 204/299, 180 R; 422/56, 57, 98

[56] References Cited

U.S. PATENT DOCUMENTS

| | | | |
|---|---|---|---|
| 3,710,933 | 1/1973 | Fulwyler | 209/3 |
| 3,815,024 | 6/1974 | Bean | 204/299 |
| 3,925,018 | 12/1975 | Saunders | 424/12 UX |
| 3,984,533 | 10/1976 | Uzgiris | 424/12 |

OTHER PUBLICATIONS

De Blois, The Rev. of Sci. Instru., vol. 41, No. 7, Jul. 1970, pp. 909–916.
De Blois, G.E. Tech. Information Ser. Report No. 76CRD192, Nov. 1976, 19 pp..

*Primary Examiner*—Anna P. Fagelson
*Attorney, Agent, or Firm*—Nathan D. Herkamp; Joseph T. Cohen; Paul R. Webb, II

[57] ABSTRACT

In a mixture of two antibody-coated latex particle suspensions, the particles in each suspension being of a different size, respectively, absence of antigen specific to the antibody in the mixture leaves multiplets only of one and the other sizes of particles. Presence of antigen in the mixture results in large particle/small particle coupling, which is detected by the resistive pulse method and indicates that an antigen-antibody reaction has occurred.

10 Claims, 2 Drawing Figures

ANTIGEN-ANTIBODY REACTION ASSAY EMPLOYING PARTICLE AGGREGATION AND RESISTIVE PULSE ANALYSIS

INTRODUCTION

This invention relates to electronic assays of protein reactions, and more particularly to a method and apparatus for detecting such reactions by sensing aggregation of protein-coated particles using a resistive pulse method.

An antigen-antibody assay based on the resistive pulse method can be of significant clinical interest because of its potential for detecting small quantities of antigen in a patient's serum. A sensitivity close to that of radio-immune assay, the standard of currently achievable sensitivity in clinical usage, can be achieved by use of the resistive pulse method.

In conventional practice of the resistive pulse method for detecting antigen-antibody reactions, latex particles are coated with antibody and the initial aggregation of the particles in the presence of antigen is observed by counting the increase in the relative number of particle multiplets. Small increases in the relative number of dimers, trimers, etc. provide a sensitive measure of the antigen-antibody reaction, and the resistive pulse method is ideally suited for measuring particle and particle multiplet size distributions. High sensitivity to small amounts of antigen can thereby be achieved.

One of the chief limitations on sensitive detection of small amounts of antigen is the false indication contributed by existence of multiplets in the particle suspension prior to the addition of antigen. These multiplets arise as a result of the procedures used to prepare the particles with antibody attached on their surfaces; that is, agglomerations of antibody-coated particles in suspension occur when the suspension is formed.

We have found that the resistive pulse method of particle detection is eminently capable of accurately measuring particle size distributions, while avoiding interference in analysis from measurement of the multiplets in unreacted particle suspensions. To make these accurate measurements, two particle suspensions are prepared, the particles in each being coated with the same antibody but the individual particles in one suspension being of larger volume that the individual particles in the other suspension by a predetermined factor. In the absence of antigen specific to the antibody coatings, a mixture of the two particle suspensions will contain multiplets of one and of the other type of particles, but no combinations of the two types of particles. Thus if, for example, an individual particle volume ratio of 1½ to 1 for the two different particle suspensions, respectively, is employed, one would expect to see in a mixture of such suspensions particles and particle multiplets with volumes of 1, 2, 3, 4 ... and 1½, 3, 4½ ..., when the volumes are in units of the smaller individual particle volume employed in the starting particle suspensions. However, we have discovered that in the presence of antigen a large particle-small particle coupling occurs in the mixture. This results in capability of obtaining a resistive pulse signal at a particle multiplet volume of 2½, which is a particle multiplet (as well as particle) volume that would be nonexistent in the absence of antigen. The resistive pulse signals obtained from particle multiplet volumes of 2½ is thus an indication of an antibody-antigen interaction and is as free of background interference as if the test were performed with only a single particle size and without initial multiplets. Hence this invention makes it possible to improve significantly the sensitivity of the resistive pulse method for detecting immunological reactions.

Accordingly, one object of the invention is to provide a method and apparatus for detecting, with high sensitivity, occurrence of an immunological reaction.

Another object is to improve the sensitivity of the resistive pulse method in detecting immunological reactions.

Another object is to provide a simple, clinical technique for detecting an antigen-antibody reaction.

Briefly, in accordance with a preferred embodiment of the invention, a method for detecting occurrence of an antigen-antibody reaction comprises preparing a first suspension of particles of a first predetermined size, each particle of the first suspension being coated with a layer of a first protein, and preparing a second suspension of particles of a second predetermined size, each particle of the second suspension being coated with a layer of the first protein. The second predetermined size is greater than one and less than two times the volume of the first predetermined size. The first and second suspensions are thereafter combined into a mixture together with a solution to be tested for presence of a second protein specific to the first protein. Multiplets of particles are then sought to be detected wherein each multiplet is formed by aggregation of a particle of the first predetermined size with a particle of the second predetermined size. If the first protein is an antibody, the second is an antigen, and vice-versa.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawings in which:

DESCRIPTION OF TYPICAL EMBODIMENTS

In practicing the invention, two separate particle suspensions are prepared, the particles in each being coated with the same antibody. The suspensions thus formed are electrically conductive because of salt and protein content. The first suspension is prepared by depositing the antibody on latex spheres conveniently of 175 nanometers diameter, dialyzed to remove surfactants and other contaminants. This may be accomplished by stirring the particles in, for example, a glycerine solution which may contain an immunoglobulin-G antibody. The second suspension is prepared by depositing the antibody on latex spheres conveniently of 200 nanometers diameter, also dialyzed to remove surfactants and other contaminants, by stirring the particles in a solution of the same composition. The two suspensions are then mixed together with a solution to be tested for presence of antigen, and the resulting conductive mixture is then tested for presence of antigen in the manner described, infra.

Choice of latex particle size is critical to proper operation of the invention. A particle volume ratio of between 1 and 2 to 1, advantageously 1½ to 1 for the two different particle suspensions, is satisfactory, although other combinations of particle sizes may be useful as well. In absence of antigen in the solution, specific to the antibody, multiplets of one and of the other types of particles are formed, respectively, but no combinations of the two types of particles occur. The solution thus contains only particles and particle multiplets with individual volumes of 1, 2, 3, 4 etc. and 1½, 3, 4½, etc. However, in the presence of antigen, a large particle-small particle coupling occurs. A resistive pulse signal can thus be detected at a multiplet volume of 2½, indicative of an antibody-antigen interaction, by employing the apparatus shown in FIG. 1.

Figure 1:
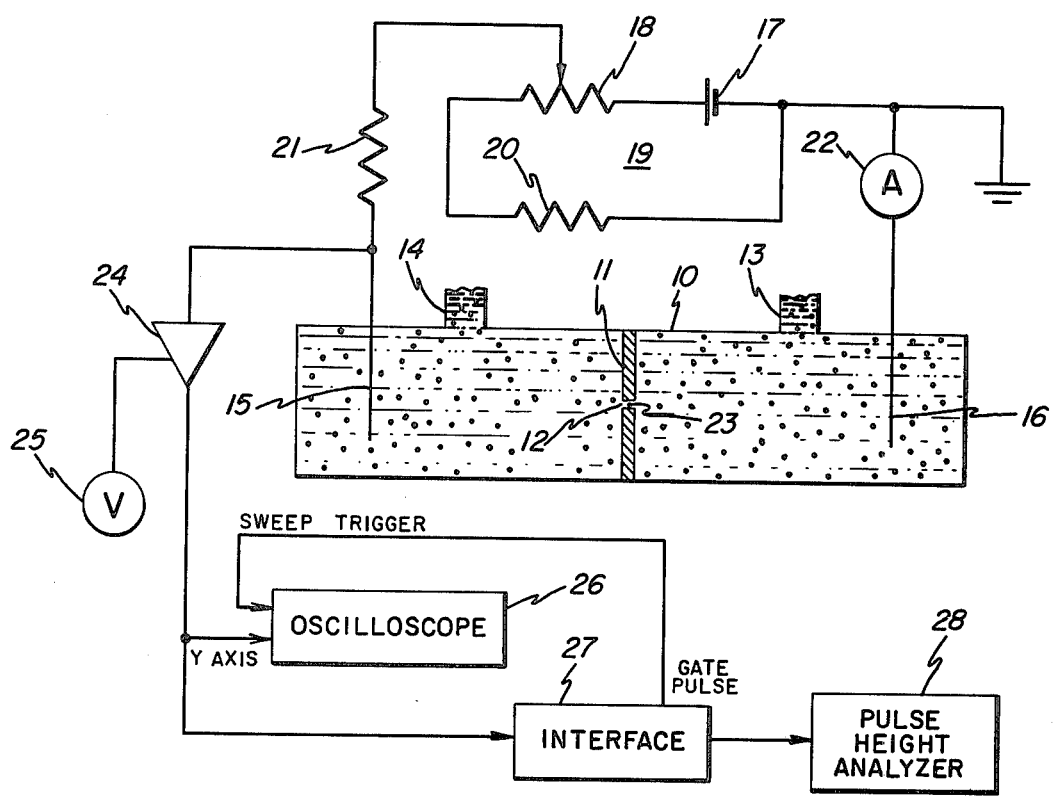
FIG. 1 is a schematic diagram of the apparatus employed in detecting an antigen-antibody reaction by the resistive pulse method where the reaction produces particle aggregation in the manner described herein.

In FIG. 1, a cell 10 comprised, for example, of a resinous material such as Plexiglas, is separated into two chambers, each approximately one cubic centimeter in volume, by a nonconductive membrane comprising a sheet of cast polycarbonate 11 containing a single pore 12, typically several tenths of a micrometer in diameter and several micrometers long. Fabrication of a polycarbonate sheet containing such pore is described by R. L. Fleischer et al. in "Novel Filter for Biological Materials", Science, 143, 249–250, January, 1964. Pore 12 is of sufficient size, typically between approximately 0.3 and 10 micrometers in diameter, to admit, individually, multiplets of the latex particles in the solution. The solution to be analyzed is caused to flow through pore 12 by applying pressure to one of the chambers through one of filling tubes 13 and 14. Silver-silver chloride electrodes 15 and 16 are contained in the cell on each side, respectively, of membrane 11.

A voltage from a d.c. supply 17, such as a battery, is applied across electrode 15 and 16 through a potential divider 19 comprised of a rheostat 18 and current-limiting resistance 20 connected in series with the d.c. supply. A load resistance 21 in series with electrode 15 is selected to be large enough (e.g., from one to several gigaohms) to render the apparatus almost a constant current system as indicated by a nanometer 22 connected in series with electrode 16. Consequently, a flow of substantially constant current is induced in the solution between electrodes 15 and 16, passing longitudinally through pore 12.

Particles, either singly or aggregated, are generally driven through pore 12 by the combined effects of applied pressure, electroosmosis and electrophoresis. A particle or multiplet 23 entering pore 12 displaces some of the conducting fluid in the pore. Since the latex particle is relatively nonconducting, as it passes longitudinally through pore 12 it increases the electrical resistance of the pore and the voltage across the pore, as measured along the direction of passage through the pore. The resulting voltage pulse across the pore is detected by electrode 15 and then amplified by a high impedance (i.e., greater than $10^{11}$ ohms) amplifier 24, such as a model MPA-6, sold by Transidyne General Corporation, Ann Arbor, Mich., which also permits the cell voltage to be read from a voltmeter 25 connected in the amplifier circuit.

The voltage pulses produced across the pore are monitored on a storage screen oscilloscope 26, such as a 5103/D11, with 5A20N and 5A15N amplifiers and 5B10 time base, sold by Tektronix, Inc., Beaverton, Oreg. The voltage pulses, which vary in amplitude in accordance with size of the particle or multiplet passing through pore 12, are also supplied to an interface 27 that converts each pulse amplitude to a several microsecond-long pulse of proportionate amplitude which is suitable for furnishing to a pulse-height analyzer 28, such as a model NS710, sold by Northern Scientific, Inc., Middleton, Wis. Interface 27 may thus constitute a sampling circuit producing an output pulse that is simply an amplified version of the sampled amplitude of the input pulse applied thereto. Pulse height analyzer 28 provides a convenient visual and quantitative readout of the output pulses from interface 27.

Interface 27 is set to sample only those pulses which exceed a predetermined amplitude threshold. Thus when a pulse applied to interface 27 reaches this threshold amplitude level, a gate pulse initiated by the interface triggers the sweep of oscilloscope 26. Amplitude sampling of the pulse applied to interface 27 occurs thereafter.

Figure 2:
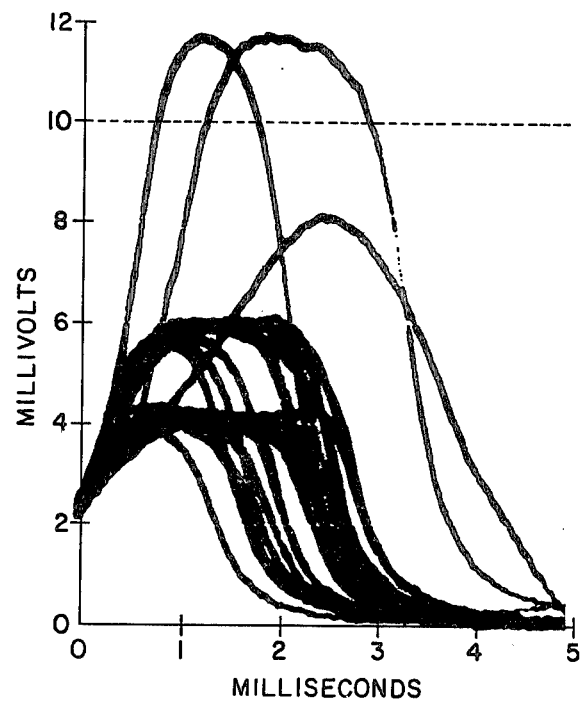
FIG. 2 is a graphical illustration of voltage pulses produced by passage of particles of different sizes, and by passage of three particle aggregations, through a single pore in the membrane employed in the apparatus of FIG. 1.

The pulses being analyzed are monitored on the screen of oscilloscope 26. FIG. 2 illustrates a number of pulses displayed on the screen of the oscilloscope during passage of particles and particle aggregates through pore 12 in the apparatus of FIG. 1. Several of these pulses are of amplitudes of approximately 4 millivolts and 6 millivolts, corresponding to passage of particles of about 500 and 570 nanometers diameter, respectively, through a 1.9 micrometer diameter pore. Additionally, two 12 millivolt pulses are displayed, corresponding probably to passage of two dimers of the 570 nanometer diameter particles (although either or both pulses might possibly correspond to passage of trimers of the 500 nanometer diameter particles), and one 8 millivolt pulse is displayed, corresponding to passage of a dimer of the 500 nanometer diameter particles. In the presence of an immunological reaction, dimers of combined 500 and 570 nanometer particles would form and show up as pulses of amplitude near 10 millivolts (as indicated by the dotted line). In this instance, the number of pulses showing up near 10 millivolts in amplitude on a pulse height histogram would be a measure of the strength of the immunological reaction.

Although in the interests of brevity in describing the invention the foregoing description specifies use of antibody-coated latex particles for detecting presence of antigens, those skilled in the art will recognize that the invention is equally applicable to use of antigen-coated latex particles for detecting presence of antibodies.

The foregoing describes a method and apparatus for detecting, with high sensitivity, occurrence of an immunological reaction. The invention serves to improve the sensitivity of the resistive pulse method in detecting immunological reactions, and constitutes a simple, clinical technique for detecting such reactions.

While only certain preferred features of the invention have been shown by way of illustration, many modifications and changes will occur to those skilled in the art. It is, therefore, to be understood that the appended claims are intended to cover all such modifications and changes as fall within the true spirit of the invention.

We claim:

1. A method for detecting occurrence of an antigen-antibody reaction, comprising:

preparing a first suspension of particles of a first predetermined size, each particle of said first suspension being coated with a layer of a first protein;

preparing a second suspension of particles of a second predetermined size, each particle of said second suspension being coated with a layer of said first protein, the second predetermined size being greater than one and less than two times the volume of the first predetermined size;

combining into a mixture said first and second suspensions together with a solution to be tested for presence of a second protein specific to the first protein; and detecting multiplets of particles to identify multiplets having a size formed only by aggregation of a particle of said first predetermined size with a particle of said second predetermined size.

2. The method of claim 1 wherein said first protein comprises an antibody and said second protein comprises an antigen specific to said antibody.

3. The method of claim 1 wherein the step of detecting said multiplets of particles comprises:

inducing a flow of substantially constant current longitudinally through a region containing a small portion of said mixture;

forcing said mixture to flow longitudinally through said region; and monitoring the voltage longitudinally across said region as said mixture flows therethrough to detect voltage pulses of predetermined amplitude as an indication of presence of said multiplets formed by aggregation of a particle of said first predetermined size with a particle of said second predetermined size.

4. The method of claim 1 wherein said particles of said second predetermined size are each of substantially $1\frac{1}{2}$ times the volume of said particles of said first predetermined size.

5. The method of claim 2 wherein said particles of said second predetermined size are each of substantially $1\frac{1}{2}$ times the volume of said particles of said first predetermined size.

6. The method of claim 3 wherein said particles of said second predetermined size are each of substantially $1\frac{1}{2}$ times the volume of said particles of said first predetermined size.

7. The method of claim 3 including the step of dividing said region into two portions joined by a passageway of between 0.3 and 10 micrometers in diameter.

8. The method of claim 6 including the step of dividing said region into two portions joined by a passageway of between 0.3 and 10 micrometers in diameter.

9. The method of claim 1 wherein said first protein comprises an antigen and said second protein comprises an antibody specific to said antigen.

10. The method of claim 9 wherein said particles of said second predetermined size are each of substantially $1\frac{1}{2}$ times the volume of said particles of said first predetermined size.

* * * * *